US00PP31360P3

(12) United States Plant Patent
Tonies

(10) Patent No.: US PP31,360 P3
(45) Date of Patent: Jan. 14, 2020

(54) ***PHLOX* PLANT NAMED 'DITOPIWI'**

(50) Latin Name: *Phlox paniculata*
Varietal Denomination: Ditopiwi

(71) Applicant: Ditoplant Export BV, Noordwijkerhout (NL)

(72) Inventor: Hubertus Josephus Tonies, Noordwijkerhout (NL)

(73) Assignee: DITOPLANT EXPORT BV, Noordwijkerhout (NL)

( * ) Notice: Subject to any disclaimer, the term of this patent is extended or adjusted under 35 U.S.C. 154(b) by 0 days.

(21) Appl. No.: 15/932,085

(22) Filed: Jan. 31, 2018

(65) Prior Publication Data

US 2019/0239409 P1 Aug. 1, 2019

(51) Int. Cl.
*A01H 5/02* (2018.01)
*A01H 6/70* (2018.01)

(52) U.S. Cl.
USPC ..... Plt./320
CPC ..... *A01H 6/70* (2018.05)

(58) Field of Classification Search
USPC ..... Plt./320
CPC ..... A01H 5/02
See application file for complete search history.

(56) References Cited

PUBLICATIONS http://www.griffins.com/pdf/plants/Phlox%20Sweet%20Summer%20Series%20Flyer%202017.pdf; 2017; 2 pages.*

* cited by examiner

*Primary Examiner* — Kent L Bell
(74) *Attorney, Agent, or Firm* — Penny J. Aguirre

(57) ABSTRACT

A new and distinct cultivar of *Phlox* plant named 'Ditopiwi', characterized by its compact and upright plant habit; freely branching and flowering habit; dark buds before flowering; large and fragrant flowers having pink eyes; dark green foliage; and a greater disease resistance than an average *Phlox paniculata.*

2 Drawing Sheets

Latin name of the genus and species of the plant claimed: *Phlox paniculata*, commonly known as garden *phlox.*

Varietal denomination: 'Ditopiwi'.

Botanical name by genus and species: *Phlox paniculata.*

BACKGROUND

The claimed plant is a new and distinct cultivar of the *Phlox* plant, botanically known as *Phlox paniculata*, and hereinafter referred to by the name 'Ditopiwi' or "the new *Phlox.*"

The parents of 'Ditopiwi' are unknown, but the parents are selections of different plants of *Phlox* Sweet Summer in a planned breeding program in a controlled environment in Noordwijkerhout, The Netherlands.

Plants of the aforementioned *Phlox* Sweet Summer breeding program have mostly dark green foliage, stems, and buds. Plants of the *Phlox* Sweet Summer breeding program also have the characteristic of easily/freely branching with a compact upright habit, which can be more useful for pot culture than an average *Phlox paniculata.* Also, plants of the *Phlox* Sweet Summer breeding program are more disease resistance than an average *Phlox paniculata*, which is one of the goals of the breeding program. Plants of the *Phlox* Sweet Summer breeding program also have large fragrant flowers and strong stems, compared to an average *Phlox paniculata.*

The claimed plant thus has dark green foliage, stems, and buds, and includes the characteristic of easily/freely branching with an upright habit. The claimed plant has large flowers (including flowerhead), and fragrant flowers. The claimed plant is more disease resistant than an average

*Phlox paniculata*. The claimed plant can be most closely compared to the *Phlox paniculata* cultivar 'Rijnstroom' (not patented). 'Rijnstroom' differs from 'Ditopiwi' in having less branching and in having flowers that are deeper pink in color with less distinguished center.

The claimed plant originated from a cross-pollination in Noordwijkerhout, The Netherlands in July 2011 of unnamed seedling selections of *Phlox paniculata* (not patented) with seeds pooled. The claimed plant was discovered and selected by the Inventor as a single flowering plant from within the progeny of the stated cross-pollination in a controlled environment in Noordwijkerhout, The Netherlands in July 2012. Asexual reproductions of the claimed plant by cuttings in a controlled environment in Noordwijkerhout, The Netherlands since 2013 have shown that the claimed plant is stable, where clones or propagules of the claimed plant are identical to the original plant in all distinguishing characteristics.

SUMMARY

The claimed plant has not been observed under all possible environmental conditions. The phenotype may vary somewhat with variations in environment and cultural practices such as temperature and light intensity without, however, any variance in genotype.

The following traits have been repeatedly observed and are determined to be unique characteristics of 'Ditopiwi'. These characteristics in combination distinguish 'Ditopiwi' as a new and distinct cultivar of *Phlox:*

1. Plants of the new *Phlox* have larger flowers (and flowerhead) relative to other plants of the botanical class.
2. Plants of the new *Phlox* have more fragrant flowers relative to other plants of the botanical class.
3. Plants of the new *Phlox* have a more compact branching growing habit relative to other plants of the botanical class.
4. Plants of the new *Phlox* have more of a dark green foliage, dark buds, and improved healthiness in comparison with other plants of the botanical class.
5. Plants of the new *Phlox* have more branching compared to *Phlox paniculata* 'Rijnstroom'.

BRIEF DESCRIPTION OF THE PHOTOGRAPHS

The accompanying colored photographs illustrate the overall appearance of the new *Phlox*, showing the colors as true as it is reasonably possible to obtain in colored reproductions of this type. Colors in the photographs may differ slightly from the color values cited in the detailed botanical description, which accurately describe the colors of the new *Phlox*.

FIG. 1 shows a top, side perspective view of a typical plant of 'Ditopiwi' grown in a 10.5 cm container.

FIG. 2 shows a close-up view of typical flowers of 'Ditopiwi'.

DETAILED BOTANICAL DESCRIPTION

The aforementioned photographs describe plants grown in Enkhuizen, The Netherlands, under commercial testing practice during the summer in containers in an outdoor nursery. During the production of the plants, day temperatures ranged from 12° Celsius to 30° Celsius, and night temperatures ranged from 2° Celsius to 16° Celsius. The plants were propagated by cuttings and were growing in a container for four months when the photographs were taken and the botanical data collected. In the following description, descriptions of color are made with reference to The Royal Horticultural Society Colour Chart, 2001 Edition, except where general terms of ordinary dictionary significance are used.

Botanical classification: *Phlox paniculata* 'Ditopiwi'.

Parentage:

*Female, or seed, parent*.—Unnamed selection of *Phlox paniculata*, not patented.

*Male, or pollen, parent*.—Unnamed selection of *Phlox paniculata*, not patented.

Propagation:

*Type*.—By cuttings.

*Time to initiate roots*.—About 3 weeks at 18° Celsius to 24° Celsius.

*Time to produce a rooted young plant*.—About 40 days at 18° Celsius to 24° Celsius.

*Root description*.—Fibrous and thin, having a pale cream tan color.

*Rooting habit*.—Moderate branching that is fairly dense.

*Disease and pest resistance*.—Has shown resistance to powdery mildew (specific agents unknown), no susceptibility or resistance to pests have been observed.

Plant description:

*Plant form/habit*.—Compact and upright habit, with a moderately vigorous growth habit that makes this plant an excellent candidate for pot growing culture.

*Branching habit*.—Freely branching habit with about four lateral branches per plant; pinching enhances branching but will delay flowering for about three weeks.

*Plant height*.—About 45 cm in a pot, and 60 cm in a garden.

*Plant width*.—About 30 cm.

*Lateral branches*.—Length depends on growing conditions, but generally about 18 cm; diameter is about 4 mm. The internode length is about 4 cm. The branches are fairly strong. The texture of the branches is sparsely pubescent. The color is close to 143B to 143C, and near the nodes the color is close to N186A and N186B.

Foliage description:

*Arrangement*.—Opposite, simple.

*Length*.—About 12 cm.

*Width*.—About 4.3 cm.

*Shape*.—Narrowly ovate to elliptic.

*Apex*.—Acute.

*Base*.—Obtuse to attenuate.

*Margin*.—Very finely serrate.

*Texture, upper and lower surfaces*.—The upper surface is sparsely pubescent; the lower surface is smooth and glabrous.

*Venation pattern*.—Pinnate.

*Color*.—Dark green, generally. The upper surface of developing leaves is close to 144A and heavily flushed close to N186A. The lower surface of developing leaves is close to 144C and flushed close to 147A. Fully expanded leaves have an upper surface between 137A and 139A; venation close to 144B to 144C. Fully expanded leaves have a lower surface close to 137C; venation close to 144D.

*Petioles*.—Length is about 4 mm; diameter is about 4 mm. The texture of the upper and lower surface is smoot and glabrous. The color of the upper and lower surfaces is close to 146B.

Flower description:

*Flower type/habit*.—Single rotate flowers arranged in terminal compound panicles; flowers face mostly upright or are outwardly facing. Panicles are rounded and hemispherical in shape. The claimed plant has a freely flowering habit with about 70 flowers developing per inflorescence. In general, the blossoms/flowers include a large head with a plurality of pink-eyed flowers.

*Fragrance*.—Moderately fragrant; sweet and pleasant.

*Natural flowering season*.—Continuously flowering from July to September in The Netherlands.

*Postproduction longevity*.—Flowers last about ten days on the plant; flowers not persistent.

*Flower buds*.—Many dark colored buds. The height is about 2.2 cm. The diameter is about 4 mm. The shape is narrowly oblanceolate. The color is close to 72B; the lower half is close to N186C; the base is close to 145C to 145D.

*Inflorescence height*.—About 11 cm.

*Inflorescence diameter*.—About 11.1 cm.

*Flower diameter*.—About 3.5 cm.

*Flower depth*.—About 2.9 cm.

*Petals*.—Quantity per flower: typically five in a single whorl. Length from throat: about 1.7 cm. Length fused: about 2.2 cm. Lobe width: about 1.7 cm. Lobe shape: roughly spatulate. Apex: rounded. Margin:

entire. Texture, upper and lower surfaces: smooth, glabrous. Color of developing petals, upper surface: close to N74B to N74C; towards the throat, between about N66A and N74A; throat, close to 187A. Color of developing petals, lower surface: between 75A and 76A; tube, close to N77B. Color of fully expanded petals, upper surface: close to N74B to N74C; towards the throat, close to N66A and N74A; throat, close to N77B. Color of fully expanded petals, lower surface: close to 75A and 76A; tube, close to N77B.

*Sepals*.—Sepals — Quantity per flower: typically five in a single whorl, fused towards the base. Length: about 8 mm. Width: about 1.5 mm. Shape: lanceolate. Apex: narrowly apiculate. Margin: entire. Texture, upper and lower surfaces: smooth, glabrous. Color of developing and fully expanded sepals, upper surface: close to N186C; towards the base, close to 145C to 145D. Color of developing and fully expanded sepals, lower surface: close to 146C to 146D; towards the base, close to N77A.

*Peduncles*.—Length: about 7.5 cm. Diameter: about 3 mm. Strength: strong. Texture: smooth, glabrous. Color: close to 146A.

*Pedicels*.—Length: about 5 mm. Diameter: about 1 mm. Strength: strong. Texture: smooth, glabrous. Color: close to 146B and 146C.

*Reproductive organs*.—Stamens: Quantity per flower: typically five. Filament length: about 1 mm. Anther shape: oblong. Anther length: about 1.5 mm. Anther color: close to 11D. Pollen amount: scarce to moderate. Pollen color: close to 8C. Pistils: Quantity per flower: one. Pistil length: about 2 cm. Stigma shape: three-parted. Stigma color: close to 150D. Style length: about 1.8 cm. Style color: close to 187D. Ovary color: close to 143A.

*Seed/fruit*.—Seed and fruit development have not been observed.

*Winter dormancy*.—In winter dormancy, the plant is not visual.

Through a growth cycle, from the start of growing, the claimed plant has dark green foliage. The claimed plant has a strikingly compact way of growing. Before flowering, the claimed plant includes very dark colored buds that are aesthetically attractive.

In general, the claimed plant includes a vigor of compact growing, with many flowers, where the claimed plant is easy to grow. The precocity includes early flowering type.

The claimed plant is more healthy than comparable plants, at least in part due to its easy growing. The claimed plant includes a pleasant fragrance and large flowers. The claimed plant flowers earlier than most of the comparable varieties. The claimed plant includes good compact growth with enough branches to fill a pot. Just before flowering, the dark buds of the claimed plant are very attractive.

What is claimed is:

1. A new and distinct *Phlox* plant named 'Ditopiwi' as illustrated and described herein.

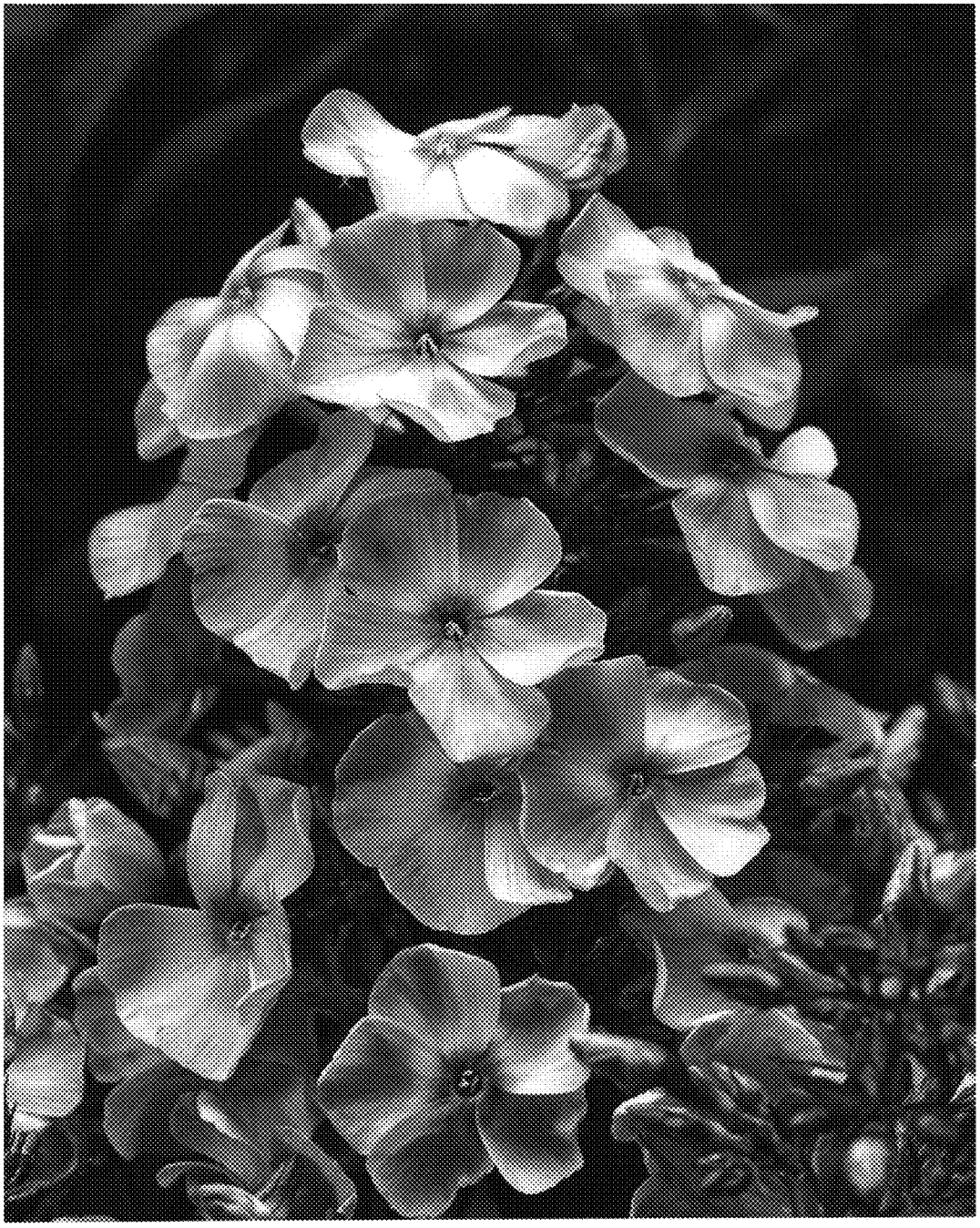

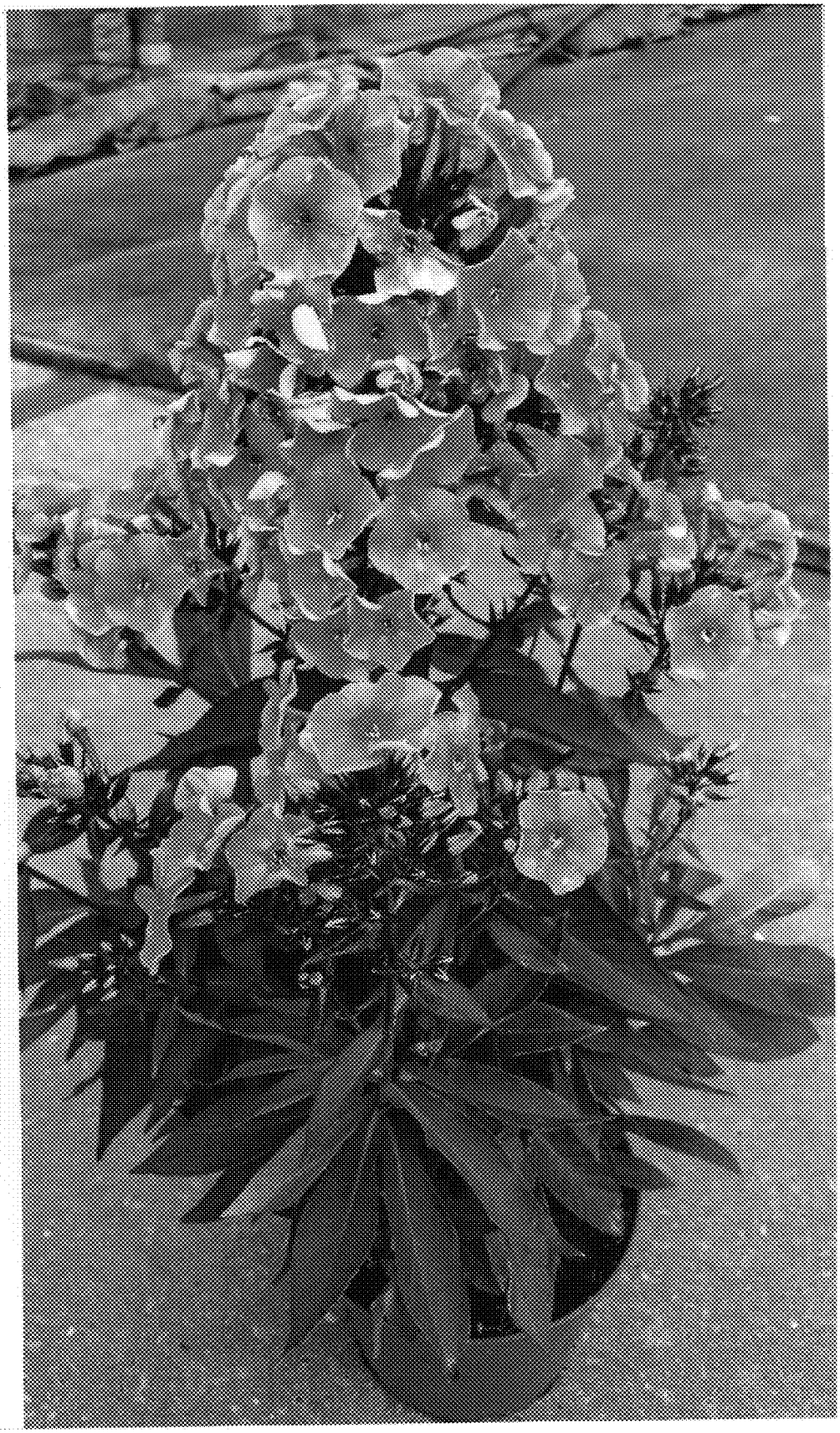

* * * * *